June 27, 1950 G. H. BUHRMAN Plant Pat. 954
AZALEA PLANT
Filed Aug. 2, 1948
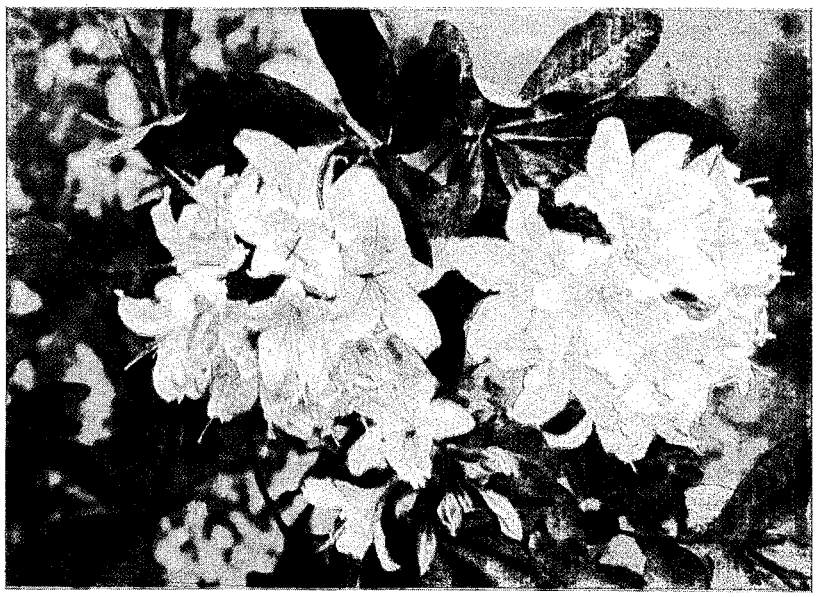
INVENTOR
GEORGE H. BUHRMAN
BY Stephen S. Townsend
ATTORNEY Patented June 27, 1950

Plant Pat. 954

UNITED STATES PATENT OFFICE

954

AZALEA PLANT

George H. Buhrman, Watsonville, Calif.

Application August 2, 1948, Serial No. 42,101

1 Claim. (Cl. 47—60)

This invention relates to a new variety of azalea and more particularly to a new variety of deciduous azalea.

The new azalea variety, subject of the present invention, is characterized by its large blooms, delicate fragrance, vigorous growth, and resistance to pest and disease. The new variety was developed through cross-breeding a member of the Mollis hybrid family, namely, the J. C. Van Tol, characterized by its bright red color, with the Occidentalis azalea which is a California native. The Occidentalis azalea blooms approximately one month subsequent to the blooming of the J. C. Van Tol and for that reason it was necessary to preserve the J. C. Van Tol by cold storage or other well known horticultural methods until such time that the Occidentalis was ready for pollenization.

The principal feature of the new variety of deciduous azalea, the subject of the present invention, is the great size of the flower which surpasses the size of a rhododendron. Average diameter of a flower of the new variety is about 3¾ inches, while I have seen flowers of the new variety up to 4½ inches in diameter.

The accompanying illustrations shows typical clusters of the flowers of the new variety in natural color.

The following is a detailed description of the new variety of deciduous azalea.

As previously noted, the size of the flower of the new variety is its principal characteristic. The average size of the bloom is approximately 3¾ inches in diameter, and is about 2 to 2½ times larger in diameter than its parent, J. C. Van Tol, and approximately 4 to 5 times larger in diameter than its parent, Occidentalis. The fragrance of the blooms of the new variety is a heavy perfumed fragrance which is not musty or disagreeable. The new variety is a sturdy grower and is resistant to disease far more so than either of its parents, the Occidentalis or J. C. Van Tol.

The plant does well in shade as well as in sunlight, and I have grown the new variety in full shade as well as in full sunlight with good results. The best results, however, are obtained where the plant is grown in partial shade which is true generally of all varieties of azaleas.

The new variety is an extremely vigorous grower and will attain a growth of 4 ft. in two years from planting. Further, the new variety will produce salable blooms within two years from planting in many instances where, normally, the Occidentalis would take four years to produce salable flowers.

The clusters of the new variety are as much as 7½ inches in diameter and average approximately 5½ inches in diameter per cluster. The blooms which form the cluster are closely compacted together to present a dense "ball." The average cluster of blooms contains approximately sixteen blooms. There may be as many as 24 clusters on a plant at approximately eight years of age, while at about four years of age there are usually between 6 to 15 clusters. Each cluster forming an excellent "ball" larger than the usual rhododendron ball.

The new variety flourishes in California and is at least equal to its parent, Occidentalis, in resistance to pests. The new variety has not been tested in other vicinities than California at the present time.

The blooming period of the new variety is from April 20th to June 1st in the Santa Clara Valley area of the State of California. On occasion blooms may appear as early as April 10th, and blooms may still be seen as late as June 15th on occasion.

The foliage of the present variety of deciduous azalea is characterized by the extreme size of the leaves which are dark green in color, darker than either of its parents. The leaves of the new variety are approximately 1 inch in width and between 4 and 5 inches in length, as a maximum. The average leaf is about ¾ of an inch in width and about 3 inches in length. The new variety is not straggly nor is it extremely compact in appearance. It is quite an erect plant and is characterized by the uniform spacing of its multiple branches. At approximately four years of age the new variety resembles in physical appearance its parent, Occidentalis, insofar as its branch spacing, but is much more gigantic than the Occidentalis. As a matter of fact, the new variety at four years of age is equavalent in size to its parent, Occidentalis, at eight years of age.

The flowers of the new variety comprise five petals, and each blossom has a dark orange blotch on the upper petal or lobe which is a characteristic of both parents of the new variety. The stamens and corrolla of the new variety are not distinguishable in form from either of its parents except that they are, of course, proportionately larger. The color of the flowers varies in accordance with the circumstances of growth, that is the color will vary according to whether the plant is grown in shade or sunlight and in accordance with the soil and care which it might receive. The color of the new variety is predominantly pink and always with the dark orange blotch as aforesaid. In some relatively few instances the color may be white with a pink rib on the petals or it may be a creamy white but always with the dark orange blotch. There is never variation in color on any individual plant. Sometimes flowers which appear on the new variety the first year may be white and the following year will turn to pink and will thereafter maintain the pink color.

The new variety is self-sterile and cannot be crossed upon itself and cannot be crossed with either of its parents, but the strain is preserved by crossing either of its parents or from cuttings from the new variety.

Having thus disclosed my invention I claim:

The variety of deciduous azalea plant herein described and illustrated characterized particularly by the large size of its flowers which grow in large compact clusters, heavy perfumed fragrance of the flowers, rapid growth, large dark green leaves, uniform spacing of its multiple branches and the predominantly pink color of its flowers and which flowers carry a dark orange blotch on the upper lobe thereof.

GEORGE H. BUHRMAN.

No references cited.